United States Patent
Clement et al.

(10) Patent No.: US 11,046,693 B2
(45) Date of Patent: Jun. 29, 2021

(54) PYRIDO-PHENANTHROLINE DERIVATIVES, PRODUCTION AND USE THEREOF AS MEDICAMENTS

(71) Applicant: Christian-Albrechts-Universitat Zu Kiel, Kiel (DE)

(72) Inventors: Bernd Clement, Kiel (DE); Christopher Meier, Kiel (DE); Tamara Natalie Steinhauer, Kiel (DE)

(73) Assignee: CHRISTIAN-ALBRECHTS-UNIVERSITÄT ZU KIEL, Kiel (DE)

( * ) Notice: Subject to any disclaimer, the term of this patent is extended or adjusted under 35 U.S.C. 154(b) by 0 days.

(21) Appl. No.: 16/465,258

(22) PCT Filed: Nov. 24, 2017

(86) PCT No.: PCT/EP2017/080327
§ 371 (c)(1),
(2) Date: May 30, 2019

(87) PCT Pub. No.: WO2018/099814
PCT Pub. Date: Jun. 7, 2018

(65) Prior Publication Data
US 2019/0292184 A1    Sep. 26, 2019

(30) Foreign Application Priority Data
Nov. 30, 2016 (EP) .................................... 16201389

(51) Int. Cl.
*C07D 471/14*    (2006.01)
*A61P 35/00*     (2006.01)

(52) U.S. Cl.
CPC ............ *C07D 471/14* (2013.01); *A61P 35/00* (2018.01)

(58) Field of Classification Search
CPC ..................................................... C07D 471/14
USPC ............................................................ 546/64
See application file for complete search history.

(56) References Cited

U.S. PATENT DOCUMENTS 9,062,054 B2 *  6/2015  Clement .............. C07D 471/14

OTHER PUBLICATIONS

West, Solid State Chemistry and Its Applications, john Wiley & Sons, 1984.*

* cited by examiner

*Primary Examiner* — Nizal S Chandrakumar
(74) *Attorney, Agent, or Firm* — Ladas & Parry LLP

(57) ABSTRACT

The invention relates to novel pyrido-phenanthroline derivatives, to the production and use thereof in the field of medicine, in particular for cancer therapy.

3 Claims, 3 Drawing Sheets

PYRIDO-PHENANTHROLINE DERIVATIVES, PRODUCTION AND USE THEREOF AS MEDICAMENTS

Figure 1:
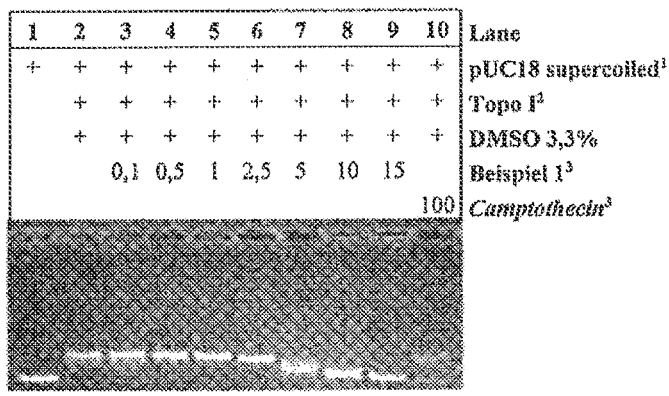

The invention relates to novel pyrido-phenanthroline derivatives, to the production and use thereof in the field of medicine, particularly for cancer therapy.

Pyrido-phenanthroline derivatives and their production are known from WO 2013/150140 A1. This patent family also describes for the first time the pharmacological, particularly anti-tumor, effect of pyrido-phenanthroline derivatives.

A promising path in the treatment of cancer is the inhibition of so-called topoisomerases, of enzymes which are needed for generating transient single and double-stranded breaks to obtain the topology of the DNA during transcription and replication as part of DNA and RNA synthesis. Inhibition of topoisomerase results in the death of the cancer cells. In therapeutical practice, inhibition of two types of topoisomerases is known: type I and type II. [http://www.cancer.gov/publications/dictionaries/cancer-terms?CdrID=46665]

Simultaneous inhibition of the two enzyme forms I and II has been found to be particularly promising for the development of new inhibiting agents of human topoisomerases in cancer therapy. A critical advantage is that upregulation of the one enzyme due to selective inhibition of the other, as is the case with currently used topoisomerase inhibitors, can be counteracted by simultaneous inhibition of both forms I and II.

Schwandt et al., for example, discuss the good efficacy of dual topoisomerase inhibitors in the treatment of small-cell lung carcinoma. [Schwandt et al.: "Brief Report: Phase II Trial of Rebeccamycin Analogue, a Dual Topoisomerase I and II Inhibitor, in Relapsed "Sensitive" SmallCell Lung Cancer" Thorac Oncol. 2012 April; 7(4): pp. 751-754). doi:10.1097/JTO.0b013e31824abca2]

Van Gijn et al. describe the efficacy of some topoisomerase inhibitors against various types of cancer, most promising are some compounds which act as dual topoisomerase inhibitors. Intoplicin, which acts as a dual topoisomerase inhibitor, shows high activity against mammary carcinoma, ovarian carcinoma, colon carcinoma, renal cell carcinoma, and non-small cell lung cancer. In clinical phase I, hepatotoxicity of the substance proved dose-limiting, which had lethal consequences for some patients. TAS-103, which also acts as a dual topoisomerase inhibitor, is effective for cancer in the head and neck, colon carcinoma, renal carcinoma, and non-small cell lung cancer; its efficacy is sufficient to keep patients stable for a period of a few months, but a cure could not be achieved. [van Gijn et al. "Dual topoisomerase inhibitors I/II" J. Oncol Pharm Practice, Vol 6, No 3(2000)].

According to Adjei et al., pyrazoloacridine (PZA, NSC 366140), a dual topoisomerase inhibitor, is effective for (metastasing) malignant melanoma, hepatocellular carcinoma, and mesothelioma. In a clinical study, patients could not be cured but were stabilized over a few months. [Adjei et al. "A phase I and pharmacologic study of pyrazoloacridine (NSC 366140) and carboplatin in patients with advanced cancer", Investigational New Drugs 20: 297-304, 2002.]

According to Grem et al., pyrazoloacridine (PZA) resulted in partial remission in at least some cases in a phase II study of pancreatic carcinoma, ovarian carcinoma, and prostate cancer. [Grem et al. "A Phase I Pharmacologic and Pharmacodynamic Study of Pyrazoloacridine Given as a Weekly 24-Hour Continuous Intravenous Infusion in Adult Cancer Patients" Clinical Cancer Research 2149 Vol. 8, pp. 2149-2156, July 2002]

De Jonge et al. describe the efficacy of dual topoisomerase inhibitor XR11576 against colon carcinoma, ovarian carcinoma, mammary carcinoma, and lung carcinoma. In-vivo xenograft studies showed high activity against colon carcinoma and non-small cell lung cancer. In clinical phase I studies, the dual topoisomerase inhibitor XR11576 showed efficacy for malignant melanoma, cervical cancer, and cancer of the parotid gland; there was stabilization, but no remission of the disease. [de Jonge et al. "Phase I and pharmacokinetic study of XR11576, an oral topoisomerase I and II inhibitor, administered on days 1-5 of a 3-weekly cycle in patients with advanced solid tumours", British Journal of Cancer (2004) 91, pp. 1459-1465]

Despite the promising approaches, no dual inhibitor could yet be used for a cytostatic therapy, which emphasizes a huge demand for new compounds from this special class of active agents.

It is therefore the object of the invention to provide novel drugs for cancer therapy.

It is further the object of the invention to provide novel compounds for inhibiting topoisomerases.

Furthermore, it is the object of the invention to provide novel compounds for simultaneously inhibiting topoisomerase type I and topoisomerase type II.

It is further the object of the invention to provide a method for producing the compounds according to the invention.

The object of the invention is solved by a compound of the formula

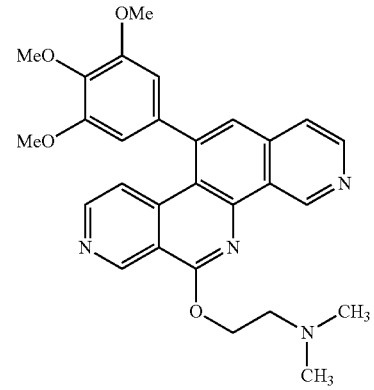 [SMILES: COc1cc(-c2cc3ccncc3c3nc(OCCN(C)C)c4cnccc4c23)cc(OC)c1OC]

6-(2-dimethylaminoethoxy)-11-(3,4,5-trimethoxyphenyl) pyrido[3,4-c][1,9]phenanthroline
as well as salts, solvates, and/or prodrugs thereof.

In a particular embodiment, the object is solved by the salt of 6-(2-dimethylaminoethoxy)-11-(3,4,5-trimethoxyphenyl) pyrido[3,4-c][1,9]-phenanthroline hydrochloride as a prodrug of 6-(2-dimethylaminoethoxy)-11-(3,4,5-trimethoxyphenyl)pyrido[3,4-c][1,9]phenanthroline as well as salts and solvates thereof, the prodrug concepts for amines known to a person skilled in the art can be used. A substitution of the tertiary amine of the side chain structure at position 6 should be carried out. The suitable prodrug concepts for such a substitution of the tertiary amine of the side chain structure at position 6 can particularly be found in [Simplicio et al, Prodrugs for Amines, Molecules, 2008, 13: 519-547]. The content of this publication is therefore expressly included herein.

The object of the invention is also solved by a method comprising the following steps:

Preparing a compound, comprising the steps
i. Reaction of the substituted benzaldehydes with 4-methylpyridine-3-carbonitrile in aprotic dipolar solvents in the presence of bases
ii. Dehydration of the product from i to a completely conjugated system, while introducing a double bond in the 11,12 position
iii. Diazotization and subsequent hydrolysis of the semicyclic amidine into a lactam structure
iv. Etherization of the lactam as in a Mitsunobu reaction For explanation, the reaction scheme shows the preparation of the synthesis steps in a specific form which does not limit the generality:

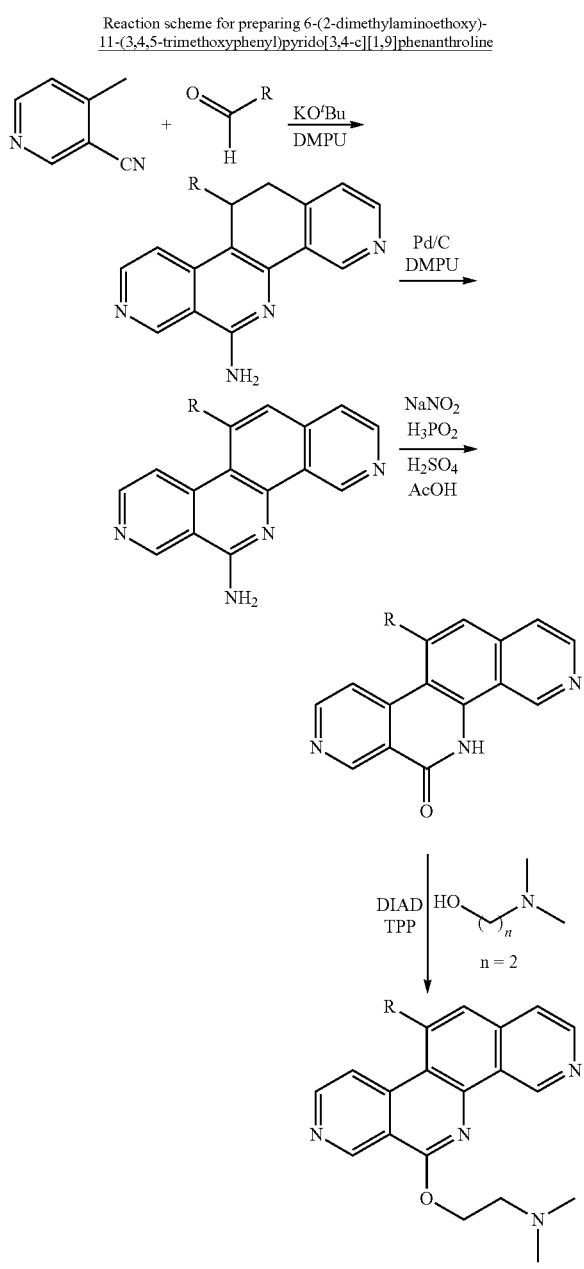

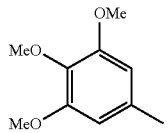

The invention also relates to drugs which contain the pyrido-phenanthroline derivative according to the invention. In addition to the phenanthroline derivative, these drugs may contain pharmaceutical adjuvants well known to a person skilled in the art, such as:

1. Fillers;
2. Binding agents;
3. Glidants;
4. Disintegrating agents;
5. Lubricants;
6. Enteric coatings; and
7. Retardants.

The compounds produced according to the invention may be incorporated in common galenic preparations such as tablets, lozenges, capsules, powders, suspensions, suppositories, or injectable solutions, optionally in combination with other active agents, and together with one or more common inert carriers and/or diluents, e.g. corn starch, lactose, cane sugar, microcrystalline cellulose, magnesium stearate, polyvinyl pyrrolidone, citric acid, tartaric acid, water, water/ethanol, water/glycerin, water/sorbite, water/polyethylene glycol, water/propylene glycol, cetyl stearyl alcohol, carboxymethyl cellulose, or fat-containing substances such as hard fat, or suitable mixtures thereof.

The invention also relates to the use of the compounds and drugs according to the invention for the treatment of diseases which can be treated with topoisomerase inhibitors. Particularly such diseases for which treatment with dual topoisomerase inhibitors has proved beneficial.

The diseases which can be treated according to the invention preferably are cancerous diseases. It is particularly preferred that the compounds and drugs according to the invention are used for treating such cancerous diseases for which dual topoisomerase inhibitors have already proved effective. Particularly preferred are the cancerous diseases treatable according to the invention selected from the group of mammary carcinomas, ovarian carcinomas, colon carcinomas, renal carcinomas, tumors of the head and neck, small-cell and non-small cell lung cancers, malignant melanomas, hepatocellular carcinomas, mesotheliomas, pancreatic cancers, prostate cancers, breast cancers, cervical cancers, and cancers of the parotid gland.

The preparation and efficacy of the compounds according to the invention will be explained below in a manner not limiting the general teaching.

Example 1

Synthesis of 6-(2-dimethylaminoethoxy)-11-(3,4,5-trimethoxyphenyl)pyrido[3,4-c][1,9]-phenanthroline Hydrochloride (Compound 1) (P8D 6)

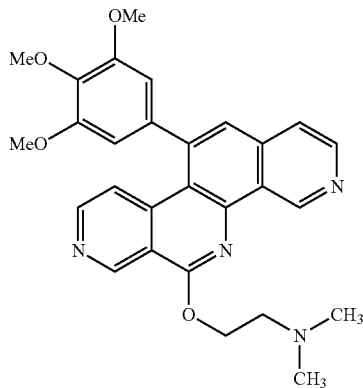

6-(2-dimethylaminoethoxy)-11-(3,4,5-trimethoxyphenyl)pyrido[3,4-c][1,9]phenanthroline The preparation of 6-(2-dimethylaminoethoxy)-11-(3,4,5-trimethoxyphenyl)pyrido[3,4-c][1,9]-phenanthroline hydrochloride (Example 1) runs through 4 stages.

Stage 1: Synthesis of 6-amino-11-(3,4,5-trimethoxyphenyl)-11,12-dihydropyrido[3,4-c]-[1,9] phenanthroline A solution of 4-methylpyridine-3-carbonitrile (500 mg, 4.2 mmol) and 412 mg (2.1 mmol) 3,4,5-trimethoxybenzaldehyde in 10 mL DMPU is added by dripping in a nitrogen atmosphere to a solution consisting of 600 mg (5.35 mmol) KotBu in 5 mL DMPU. After a reaction time of 3 hours, the reaction mixture is hydrolyzed on 80 mL ice water. The resulting precipitate is suctioned off. The crude product is purified by flash chromatography on silica gel (eluent: dichloromethane/methanol (5-20%). The solid obtained is dried for 24 h under an oil pump vacuum. Yield: 244 mg (28%).

Stage 2: Synthesis of 6-amino-11-(3,4,5-trimethoxyphenyl)pyrido[3,4-c][1,9]phenanthroline 200 mg (0.48 mmol) 6-amino-11-(3,4,5-trimethoxyphenyl)-11,12-dihydropyrido[3,4-c]-[1,9]phenanthroline are dissolved in 5-10 mL DMPU and palladium (10%) on activated carbon (30 percent by weight) is added. The suspension is heated to reflux under nitrogen flow for 10 minutes. After cooling, the catalyst is filtered off and the batch is rewashed with 50 mL dichloromethane. The filtrate is evaporated in a rotary evaporator, and the remaining solution is added to 80 mL ice water, resulting precipitate is filtered off. If no precipitate results, the pH is set to 2 with concentrated hydrochloric acid, and the DMPU is extracted from the aqueous phase with 3×50 mL dichloromethane. Then the aqueous phase is brought to pH 9 with 25% aqueous ammonia solution, and the resulting precipitate is filtered off. The crude product is purified by flash chromatography on silica gel (eluent: dichloromethane/methanol (10%). The solid obtained is dried for 24 h in an oil pump vacuum. Yield: 149 mg (75%).

Stage 3: Synthesis of 11-(3,4,5-trimethoxyphenyl)-5,6-dihydropyrido[3,4-c][1,9]phenanthroline-6-one 3 N sulfuric acid (5 mL) is cooled down to 0° C., then $NaNO_2$ (250 mg, 36 mmol) and phosphinic acid pre-cooled to 4° C. (1 mL, 1,2 mmol, 50 percent by weight in $H_2O$) are added slowly, in portions, one after the other. A second solution consisting of 300 mg (6-amino-11-(3,4,5-trimethoxyphenyl)pyrido[3,4-c][1,9]phenanthroline in 5 mL glacial acetic acid and 2 mL water is added slowly by dripping to the first solution. After adding a spatula tip of copper(II)sulfate, the solution mixture is stirred for one hour at 0° C. and then stored in the refrigerator at 4-7° C. for 24 hours. Then the solution is filtered off and the filtrate is set to pH 9 with 25% aqueous ammonia solution until a deep blue coloring occurs. The resulting precipitate is suctioned off, washed with water (3×50 mL) and dried under vacuum. The crude product is purified by flash chromatography on silica gel (eluent: dichloromethane/methanol (5-20%)). The solid obtained is dried for 24 h under an oil pump vacuum. Yield: 243 mg (81%).

Stage 4: Synthesis of 6-(2-dimethylaminoethoxy)-11-(3,4,5-trimethoxyphenyl)pyrido[3,4-c]-[1,9] phenanthroline Hydrochloride 11-(3,4,5-trimethoxyphenyl)-5,6-dihydropyrido[3,4-c][1,9]phenanthroline-6-one (300 mg, 0.73 mmol) is dissolved with triphenylphosphine (571 mg, 2.2 mmol) in 50 mL freshly dried THF. Then 2-dimethylaminoethanol (196 mg, 2.2 mmol) and DIAD *445 mg, 2.2 mmol) are added one after the other by dripping. The suspension is stirred in the absence of water for 72 hours at room temperature, which gradually results in a clear solution. After the reaction is completed, the solvent is removed in a rotary evaporator and the solid obtained is dried under vacuum. The crude product is purified by flash chromatography on silica gel (eluent: dichloromethane/methanol (10-30%), and the resulting product is thereafter dried for 24 hours under an oil pump vacuum. The product is dissolved in dry dichloromethane and gassed for 5 minutes with HCl (g). The solvent is removed in a rotary evaporator, and the solid obtained is dried for 24 hours under an oil pump vacuum.

$C_{28}H_{29}N_4O_4$ (521.01)

Yield: 274 mg (72%, precipitated as hydrochloride after purification by flash chromatography, silica gel, $CH_2Cl_2$/MeOH (10-30%)) of a yellow solid Melting point: 206° C.

$^1$H-NMR (300 MHz, DMSO-d6):

δ/ppm=2.96 (d, 6H, $RHN(CH_3)_2$), 3.74 (s, 6H, $2\times OCH_3$), 3.81 (s, 5H, $OCH_3$, H-2'), 5.33 (m, 2H, H-1'), 6.88 (s, 2H, H-2″, H-6″), 7.37 (dd, 1H, H-10, $^3J=6.2$ Hz, $^4J=0.8$ Hz), 8.28 (s, 1H, H-12), 8.56 (d, 1H, H-1, $^3J=6.3$ Hz), 8.74 (d, 1H, H-9, $^3.1=6.2$ Hz), 8.95 (d, 1H, H-2, $^3J=6.3$ Hz), 10.08 (d; 1H, H-7, J=0.7 Hz), 10.64 (s, 1H, H-4), 11.25 (m, 1H, $RHN(CH_3)_2$).

The signal of the methylene protons at C-2' is superimposed by the singlet of the methoxy group at 3.81.

$^{13}$C-NMR (75 MHz, DMSO-d6):

δ/ppm=42.5 (2C, $RHN(CH3)2$), 54.8 (C-2'), 56.2 (2C, $2\times OCH_3$), 60.4 ($OCH_3$), 61.8 (C-1'), 106.0 (2C), 115.3, 118.0, 119.2, 124.0, 124.1, 126.0, 136.1, 136.5, 138.2, 139.0, 139.6, 143.8, 144.3, 147.1, 148.9, 153.7 (2C), 159.6.

IR (ATR):
cm$^{-1}$=3399, 2946, 2467, 1639, 1606, 1578, 1453, 1412, 1338, 1111, 988.
MS (ESI):
m/z=485 ([M+H]+, 41%), 414 ([M-C4H9N+H]$^+$, 100%), 243 ([M+2H], 44%).
Elemental analysis (C$_{28}$H$_{28}$N$_4$O$_4$×3 HCl):

| Calculated: | C 56.62 | H 5.26 | N 9.43, |
| Found: | C 56.20 | H 5.52 | N 9.40. |

Example 2

Synthesis of 6-(3-dimethylaminopropoxy)-11-(3,4,5-trimethoxyphenyl)pyrido[3,4-c][1,9]-phenanthroline (Compound 2)

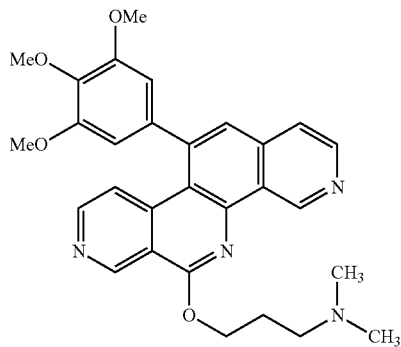 [SMILES: COc1cc(-c2cc3ccncc3c3nc(OCCCN(C)C)c4cnccc4c23)cc(OC)c1OC]

6-(3-dimethylaminopropoxy)-11-(3,4,5-trimethoxyphenyl)pyrido[3,4-c][1,9]phenanthroline The preparation of 6-(3-dimethylaminopropoxy)-11-(3,4,5-trimethoxyphenyl)pyrido[3,4-c][1,9]-phenanthroline hydrochloride (Example 2) likewise runs through 4 stages.

Stages 1 to 3 are similar to the preparation of Example 1.

Stage 4: 11-(3,4,5-trimethoxyphenyl)-5,6-dihydropyrido[3,4-c][1,9]phenanthroline-6-one (300 mg, 0.73 mmol) is dissolved with triphenylphosphine (571 mg, 2.2 mmol) in 50 mL freshly dried THF. Then dimethylaminopropanol (227 mg, 2.2 mmol) and DIAD (445 mg, 2.2 mmol) are added one after the other by dripping. The suspension is stirred in the absence of water for 72 hours at room temperature, which gradually results in a clear solution. After the reaction is completed, the solvent is removed in a rotary evaporator and the solid obtained is dried under vacuum. The crude product is purified by flash chromatography on silica gel (eluent: dichloromethane/methanol (10-30%), and the resulting product is thereafter dried for 24 hours under an oil pump vacuum.

C$_{29}$H$_{30}$N$_4$O$_4$ (498.57)

Yield: 163 mg (55%, flash chromatography, silica gel, CH$_2$Cl$_2$/MeOH (10-30%)) of a yellow solid Melting point: 172° C.

$^1$H-NMR (300 MHz, DMSO-d$_6$+1% DCl (36%) in D$_2$O):
δ/ppm=2.46 (m, 2H, H-2'), 2.83 (s, 6H, RHN(CH$_3$)$_2$), 3.49 (m, 2H, H-3'), 3.72 (s, 6H, 2×OCH$_3$), 3.78 (s, 3H, OCH$_3$), 5.07 (t, 2H, H-1'), 6.90 (s, 2H, H-2", H-6"), 7.71 (dd, 1H, H-10, $^3$J=6.6 Hz), 8.37 (s, 1H, H-12), 8.66 (d, 1H, H-1, $^3$J=6.5 Hz), 8.83 (d, 1H, H-9, $^3$J=6.6 Hz), 8.96 (d, 1H, H-2, $^3$J=6.4 Hz), 10.10 (s, 1H, H-7, J=0.7 Hz), 10.64 (s, 1H, H-4).

$^{13}$C-NMR (75 MHz, DMSO-d$_6$+1% DCl (36%) in D$_2$O):
δ/ppm=23.3 (C-2'), 42.2 (2C, RHN(CH$_3$)$_2$), 53.9 (C-3'), 56.5 (2C, 2×OCH$_3$), 60.7 (OCH$_3$), 66.0 (C-1'), 106.4 (2C), 116.9, 117.6, 122.6, 124.2, 125.0, 126.6, 135.5, 135.7, 138.7, 139.5, 140.6, 143.4, 144.1, 144.5, 146.4, 148.1, 154.1 (2C), 160.4.

IR (ATR):
cm$^{-1}$=3363, 2936, 2834, 1610, 1566, 1407, 1343, 1230, 1126, 1112, 830.

MS (ESI):
m/z=499 ([M+H]$^+$, 51%), 414 ([M-C$_5$H$_{11}$N+H]$^+$, 100%), 250 ([M+2H]$^{++}$, 73%).

HRMS (ESI):
m/z calculated for [M+H]$^+$: 499.2345,
m/z found for [M+H]$^+$: 499.2326, Example 3

Synthesis of 11-(3-chlorophenyl)-6-(2-dimethylaminoethoxy)-11,12-dihydropyrido[3,4-c]-[1,9]phenanthroline Hydrochloride (Compound 3) (P16 6)

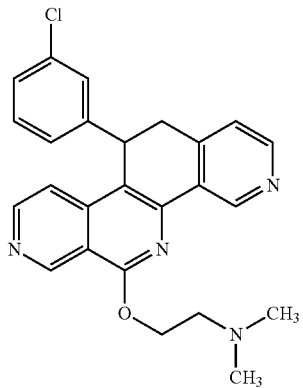 [SMILES: CN(C)CCOc1nc2c(c3ccncc13)C(c1cccc(Cl)c1)Cc1ccncc1-2]

11-(3-chlorophenyl)-6-(2-dimethylaminoethoxy)-11,12-dihydropyrido[3,4-c][1,9]phenanthroline Hydrochloride The preparation of 11-(3-chlorophenyl)-6-(2-dimethylaminoethoxy)-11,12-dihydropyrido[3,4-c][1,9]phenanthroline hydrochloride (Example 3) runs through 3 stages.

Stage 1: Synthesis of 6-amino-11-(3-chlorophenyl)-11,12-dihydropyrido[3,4-c][1,9]phenanthroline: 3-Chlorobenzaldehyde (295 mg, 2.1 mmol) is reacted analogously to the preparation instructions for stage 1 of Example 1. Yield: 241 mg (32%).

Stage 2: Synthesis of 11-(3-chlorophenyl)-5,6,11,12-tetrahydropyrido[3,4-c][1,9]phenanthroline-6-one: 300 mg (0.84 mmol) 6-amino-11-(3-chlorophenyl)-11,12-dihydropyrido[3,4-c][1,9]phenanthroline are reacted analogously to in the preparation instructions for stage 3 of Example 1. Yield: 277 mg (91%).

Stage 3: 300 mg (0.83 mmol) 11-(3-chlorophenyl)-5,6,11,12-tetrahydropyrido[3,4-c][1,9]phenanthroline-6-one are reacted analogously to the preparation instructions for stage 4 of Example 1.

$C_{25}H_{24}C_{12}N_4O$ (467.39)

Yield: 177 mg (45%, precipitated as hydrochloride after purification by flash chromatography, silica gel, $CH_2Cl_2$/MeOH (10-30%)) of a yellow solid Melting point: 188° C.

$^1$H-NMR (300 MHz, DMSO-$d_6$):

δ/ppm=2.93 (t, 6H, RHN(CH$_3$)$_2$), 3.62 (d, 1H, H-12a, $^2J_{H-12a/H-12b}$=17.2 Hz), 3.75 (q, 2H, H-2', $^3J$=5.1 Hz), 3.84 (dd, 1H, H-12-b, $^2J_{H-12b/14-12a}$=17.3 Hz, $^3J_{H-12b/H-11}$=7.9 Hz), 5.15 (m, 2H, H-1'), 5.32 (d, 1H, H-11, $^3J_{H11/H12-b}$=7.8 Hz), 6.80-6.86 (m, 1H, H-6", $^3J$=7.7 Hz), 7.14 (m, 1H, H-5", $^3J$=7.8 Hz), 7.18-7.23 (m, 1H, H-4", $^3J$=7.8 Hz), 7.30 (m, 1H, H-2"), 7.94 (d, 1H, H-1, $^3J$=5.7 Hz), 8.05 (d, 1H, H-10, $^3J$=6.4 Hz), 8.80 (d, 1H, H-2, $^3J$=5.7 Hz), 8.85 (d, 1H, H-9, $^3J$=6.3 Hz), 9.60 (s, 1H, H-4), 10.09 (s, 1H—H-7), 11.21 (m, 1H, RHN(CH$_3$)$_2$).

$^{13}$C-NMR (75 MHz DMSO-$d_6$):

δ/ppm=35.0 (C-12), 35.2 (C-11), 42.3, 42.4 (2C, RHN (CH$_3$)$_2$), 54.7 (C-2;'), 61.4 (C-1'), 114.8, 117.6, 120.8, 125.7, 126.4, 127.1, 127.3, 130.5, 131.8, 133.4, 138.5, 140.9, 142.9, 134.3, 143.7, 145.5, 148.4, 160.0.

IR (ATR):

cm$^{-1}$=3364, 2970, 2468, 1632, 1592, 1561, 1465, 1425, 1342, 829.

MS (ESI):

m/z=433 ([M+H]$^+$, $^{37}$Cl, 18%), 431 ([M+H]$^+$, $^{35}$Cl, 44%), 362 ([M-C$_4$H$_9$N+H]$^+$, $^{37}$Cl, 35%), 360 ([M-C$_4$H$_{10}$N+H]$^+$, $^{35}$Cl, 100%), 343 (3%), 248 ([M-3-chlorobenzene+H]$^+$, 6%).

HRMS (ESI):

m/z calculated for [M+H]$^+$: 431.1633, m/z found for [M+H]$^+$: 431.1613,

Pharmacological Test Results

For studying the pharmacological properties, the compounds of Examples 1 to 3 were tested under the "DTP NCI-60 in vitro human tumor cell line screening" of the National Cancer Institute (NCI), Bethesda, Md., United States. They were tested against 60 different human pathogenic tumor cell lines which originated from nine types of cancer (leukemia, non-small cell lung cancer, colon cancer, cancer of the CNS, melanoma, ovarian cancer, renal cancer, prostate cancer, breast cancer). To assess efficacy, the tumor cells were exposed to the compounds over two days, then growth inhibition was determined indirectly by determining the protein biomass with sulforhodamine B (SRB). Untreated cultures were used as reference. The mean-graph midpoint (MG_MIDG$_{GI50}$) corresponds to a mean response rate of all tested human cell lines for the substance tested. De-logarithmized, it shows the concentration which results in a 50 percent growth inhibition of all cell lines with respect to untreated reference cell lines (GI$_{50-NCI60}$). Table 1 shows the very strong growth-inhibiting action of the three compounds 1 to 3 at nanomolar concentrations on average on the 60 human tumor cell lines.

The efficacy of the exemplary compounds 1 to 3 in part clearly exceeds the growth-inhibiting properties of drugs approved for cancer therapy and model compounds from the class of topoisomerase inhibitors, which were also subjected to this testing system.

The compounds pyrazoloacridine (PZA) and intoplicin, which are already in clinical development, are listed from the class of dual topoisomerase I/II inhibitors. The compounds from Example 1 and Example 2 show much improved antitumor action, particularly if compared to the two known topoisomerase I/II inhibitors pyrazoloacridine (PZA) and intoplicin.

TABLE 1

Mean growth inhibition of all 60 tumor cell lines of the DTP NCI-60 in vitro human tumor cell screening

| Substance | GI$_{50/NCI-60}$ [μM] |
|---|---|
| Example 1 | 0.049 |
| Example 2 | 0.052 |
| Example 3 | 0.447 |
| Topo I inhibitors | |
| Camptothecin | 0.044 |
| Topotecan | 0.014 |
| Irinotecan | 0.16 |
| Topo II inhibitors | |
| Etoposide | 0.99 |
| Teniposide | 0.39 |
| Dual topo I/II inhibitors | |
| PZA | 0.20 |
| Intoplicin | 0.53 |

As part of studying their pharmacological properties, the compounds 1 to 3 were also tested for their ability to inhibit activities of human topoisomerases I, IIα, and IIβ. The respective model topoisomerase inhibitors camptothecin (topoisomerase I) and etoposide (topoisomerase II) were also tested as reference compounds. Table 2 shows the results.

TABLE 2

Inhibition of human topoisomerases I, IIα, and IIβ by Example 1:

| Substance | GI$_{50}$(topoisomerase I)$^1$ | GI$_{50}$(topoisomerase IIα)$^2$ | GI$_{50}$(topoisomerase IIβ)$^2$ |
|---|---|---|---|
| Example 1 | +++ | +++ | +++ |
| Camptothecin | + | n.d. | n.d. |
| Etoposide | n.d. | + | + |

+++: IC$_{50}$ = 10-50 μM,
+: IC$_{50}$ = 50-100 μM.
$^1$Data from the relaxation assay;
$^2$Data from the decatenation assay;
n.d. = not determined.

Exemplary compound 1 (Ex. 1) shows extraordinarily strong and uniform inhibition of the activity of all human topoisomerases in these tests (IC$_{50}$<10 μM for all three enzymes tested); inhibition was much stronger than the activities of the model topoisomerase inhibitors etoposide and camptothecin. Surprisingly, only exemplary compound 1 displayed these properties of a potent dual topoisomerase I/II inhibitor.

FIG. 1 shows the influence on topoisomerase I activity by means of a relaxation assay. A relaxation assay can be used to determine the inhibition of human DNA topoisomerase I by a substance. Topo I is capable of transforming the supercoiled plasmid pUC18 into the relaxed form. The resulting different migration characteristics of plasmid isoforms in an agarose gel when applying an electrical field provide a measure of the activity of the enzyme (Nitiss et al., Topoisomerase Assays, in: Enna et al., Curr. Prot. Pharmacol., 2012). Apparent is a concentration-dependent inhibition of topoisomerase I activity by increasing concentrations of exemplary compound 1 (lanes 3 to 9), which is almost complete at 10 μM, compared to lane 1, which contains the supercoiled plasmid without topoisomerase I. Lane 2 represents the negative control without an inhibitor. Camptothecin at a concentration of 100 μM (lane 10) was used as positive control.

Figure 2:
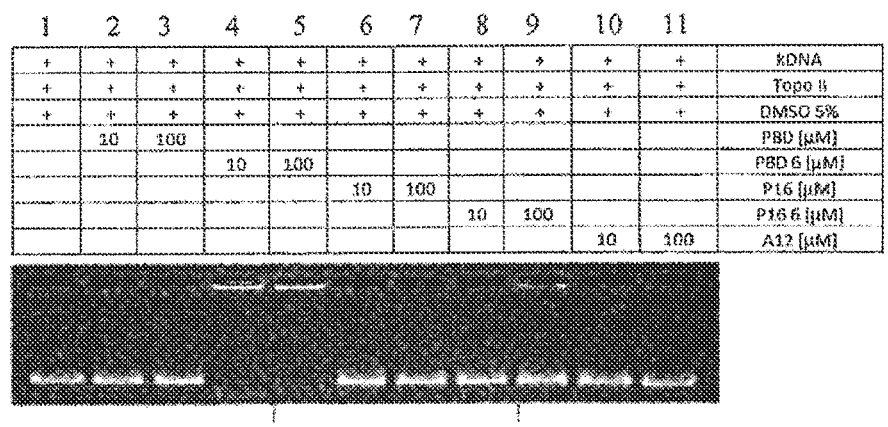

FIG. 2 shows the influence of various pyridophenanthrolines (P8D, P16, P16 6 (corresponds to compound 3 from Example 3), and P8D 6 (corresponds to compound 1 from Example 1) and of pyridoazacarbazole A12 on the enzyme as examples of inhibiting topoisomerase IIα activity.

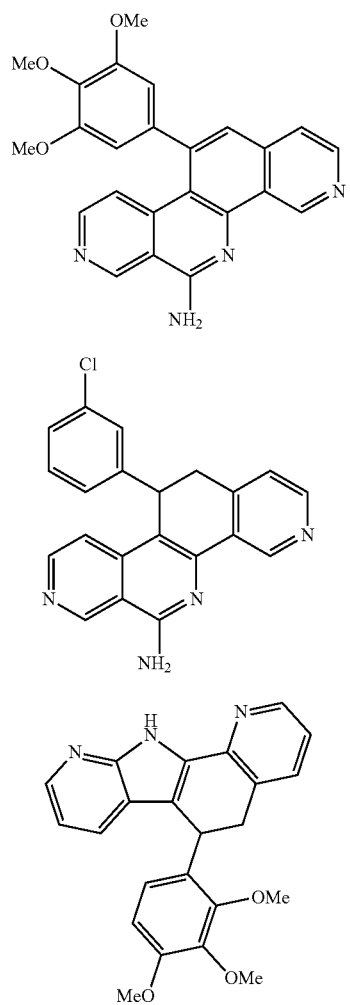

A decatenation assay was used, which can be used to determine the inhibition of human topoisomerases II (α/β) by a substance. The protein is capable of decatenating kinetoplastid DNA (kDNA), which is present in the form of interlocked minicircles (so-called catenates), i.e. of cleaving it into individual minicircles. Unlike the original kDNA, these can migrate in an agarose gel when applying an electrical field (Nitiss et al., Topoisomerase Assays, in: Enna et al., Curr. Prot. Pharmacol., 2012).

FIG. 2 shows how only exemplary compound 1 (P8D 6) was able to potently inhibit topo IIα, such that no unlocked DNA minicircles were formed, which can be seen from the immobility of the bands in lanes 4 and 5, compared to lane 1, which is shown here as reference without an inhibitor.

Only example 1 was able, against expectations, to achieve exemplary inhibition of topo IIα both in the low (10 μM) and high (100 μM) concentration ranges.

Figure 3:
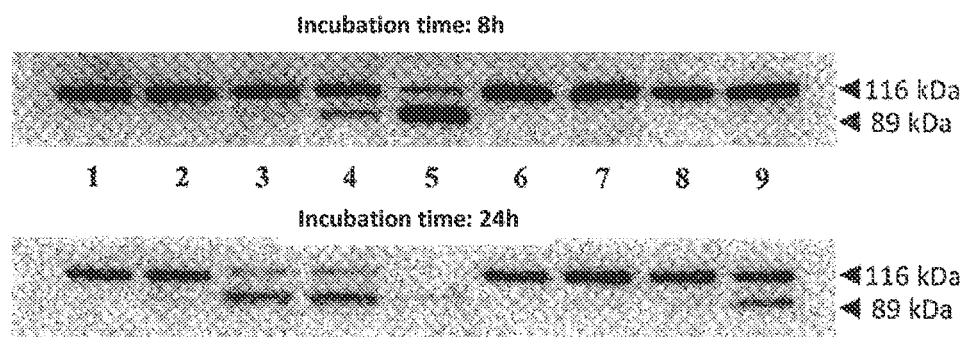

In addition, exemplary compound 1 was tested for apoptotic activity. The enzyme PARP (poly-ADP ribose polymerase) can be used to determine the apoptotic status of a cell; the enzyme is cleaved into a 89 kDa fragment when the cell transitions into apoptosis and can therefore serve as a apoptosis marker (KAUFMANN S H et al, Cancer Research, 1993; 53:3976-3985). FIG. 3 shows the effect of various concentrations of Example 1 on HeLa cells in the PARP assay. Etoposide was chosen as reference compound and tested as well.

FIG. 3 shows very fast occurrence of the apoptotic state of the cell (89 kDa band—cleaved PARP already at a concentration of 1 μM visible on exemplary compound 1, no initiation of apoptosis for etoposide ≤100 μM after 8 h). After 24 h, a concentration of exemplary compound 1 which is by $10^3$-$10^{-2}$ times lower than that of etoposide is sufficient to detect the PARP cleavage product. Exemplary compound 1 therefore has an excellent apoptotic effect.

Figure 4:
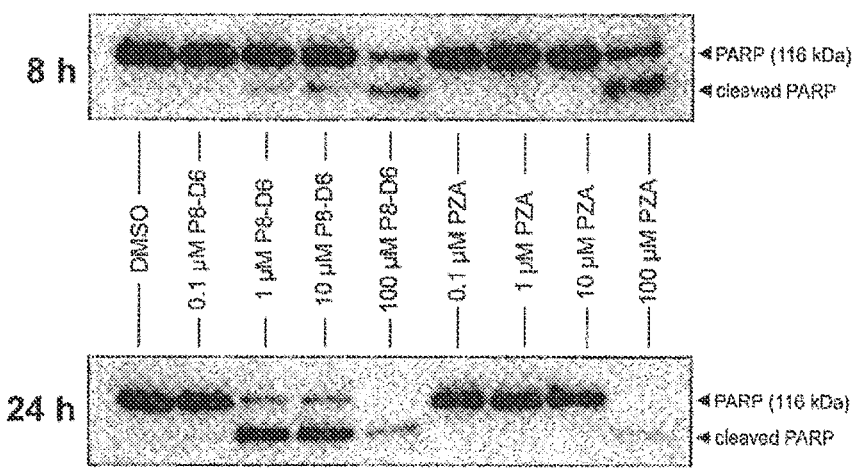

Another PARP assay was performed to obtain a direct comparison of the pro-apoptotic effects of Example 1 (here: P8D 6) and the potent dual topoisomerase I/II inhibitor pyrazoloacridine (PZA) known from literature (FIG. 4).

This also illustrates the extraordinarily strong apoptotic effect of exemplary compound 1, while the dual topoisomerase inhibitor PZA is effective only at high concentrations (100 μM).

Physical and Chemical Properties:

In addition to excellent pharmacological properties, the compounds display physical and chemical advantages, which further emphasize their excellent suitability as drugs (Table 3).

TABLE 3

Physical and chemical properties of exemplary compounds 1-3:

| Substance | Solubility pH 7.4 [mM][1] | H donors[2] | H acceptors | logD[1]/ Clog P[3] | Molecular weight [g/mol] |
|---|---|---|---|---|---|
| Example 1 | 0.87 ± 0.03 | 1 | 8 | 3.70/4.08 | 485 |
| Example 2 | n.d. | 1 | 8 | 3.60/4.43 | 499 |
| Example 3 | 5.28 ± 0.09 | 1 | 5 | 3.60/5.13 | 431 |

Table 3: Physical and chemical properties of exemplary compounds 1-3;
[1]Determined using HPLC analysis;
[2]The tertiary amine structure was considered protonated at pH 7.4;
[3]Calculated using ChemDraw Ultra 12.0.

Solubility in the millimolar range and applicability of the "rule of five" (based on: LIPINSKI C A et al., Advanced Drug Delivery Reviews, 2001; 46: 3-26) predict adequate oral bioavailability for exemplary compounds 1 to 3, which therefore allows peroral administration of these compounds in addition to the parenteral application which is common for cytostatics.

Toxicological Properties:

Tolerability of Exemplary Compound 1 (Here: P8-D6) in Female Athymic Nude Mice

Study Design

Internal study number: P14.0073. The animal experiment, which was carried out under internal study number P 14.0073, was approved by the local government authority and the associated ethics committee (Karlsruhe Regional Council, 35-9185.81/G-24/11).

The maximum tolerated dose (MTD) was determined as part of an in vivo study of tolerability of P8-D6 in female athymic nude mice.

A total of 18 female athymic nude mice at ages of 7 weeks (groups 1 and 2), 8 weeks (groups 3 and 4), and 9 weeks (groups 5 and 6) were involved in the in vivo study.

To determine the tolerability of P8-D6 for a one-time intravenous application into the tail vein, the study animals of groups 2, 4, and 6 (3 animals per group) were given P8-D6 at doses of 1 mg/kg body weight, 5 mg/kg body weight, and 10 mg/kg body weight on study days 0, 7, and 14, respectively. The control animals of groups 1, 3, and 5 (3 animals per group) were administered PBS (phosphate buffered saline) (pH 7.4) at a dose of 10 mL/kg body weight on the same respective days. The study animals were monitored in a period of up to 14 days for clinical signs, changes in behavior, and survival. The body weight was measured three times a week. The first measurement was on the application day. Criteria for early abortion of the study for ethical reasons were weight loss of more than 20% from the baseline weight. A necropsy was performed on study animals that died during the study and on all other study animals at the end of the study phase. Organ samples were taken from six study animals (4 animals from group 4, 1 animal from group 1, 1 animal from group 2, and one animal from group 6).

Findings

Figure 5:
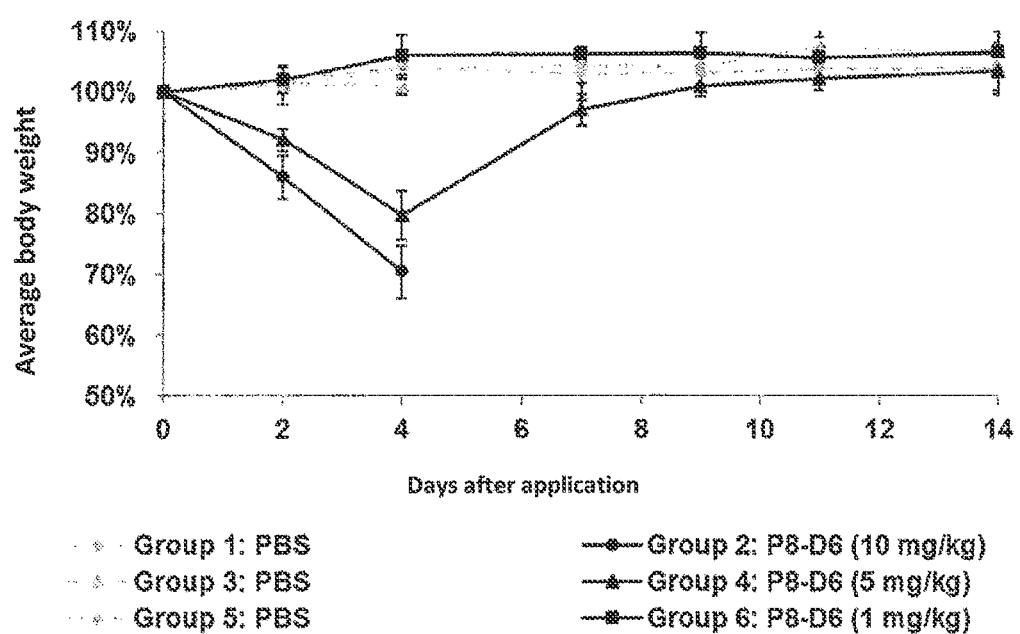

FIG. 5 shows the findings after one-time intravenous application of P8D 6 to female athymic nude mice and intravenous administration of PBS for comparison.

The MTD study showed good tolerability of P8-D6 in female athymic nude mice at a dosage of 1 mg/kg body weight. Furthermore, dose-dependent toxicity at higher concentrations was determined based on clinical signs and monitoring the body weight, wherein the loss of body weight and occurring apathy of the study animals were reversible at a dose of 5 mg/kg body weight (FIG. 5). None of the study animals displayed acute lethal side effects.

LIST OF FIGURES

FIG. 1: Relaxation assay for influencing the topoisomerase I activity: [1]Supercoiled plasmid pUC 18, [2]Topoisomerase I, [3]Test concentrations of exemplary compound 1. Unit: μM.

FIG. 2: Decatenation assay for influencing topoisomerase IIα activity: Lane 1 Reference without inhibitor, lanes 2 and 3 (P8D), lanes 6 and 7 (P16), lanes 8 and 9 (P16 6), and lanes 10 and 11 (Al2) are comparisons to similar structures. Lanes 4 and 5 are exemplary compound 1, lanes 8 and 9 are exemplary compound 3. kDNA=kinetoplastid DNA; Topo II=topoisomerase IIα

FIG. 3: PARP apoptosis assay (HeLa cells).1: DMSO control (no inhibitor), 2-5: Example 1 (0.1; 1; 10; 100 μM); 6-9: Etoposide (0.1; 1; 10; 100 μM).

FIG. 4: PARP assay to compare Example 1 and the dual topoisomerase I/II inhibitor pyrazoloacridine (PZA)

FIG. 5: One-time intravenous application of exemplary compound 1 (P8D 6) to female athymic nude mice and intravenous administration of PBS for comparison

The invention claimed is:

1. A compound of the formula

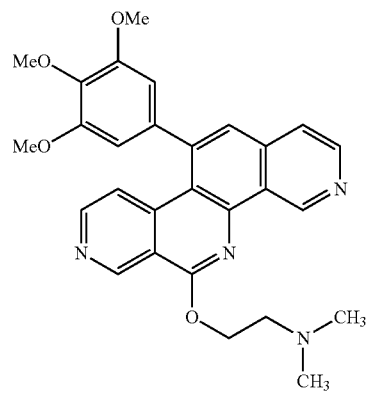 [SMILES: COc1cc(-c2cc3ccncc3c3nc(OCCN(C)C)c4cnccc4c23)cc(OC)c1OC]

as well as salts thereof, for simultaneously inhibiting topoisomerase type I and topoisomerase type II.

2. The compound according to claim 1, characterized in that it is 6-(2-dimethylaminoethoxy)-11-(3,4,5-trimethoxyphenyl)pyrido[3,4-c][1,9]-phenanthroline hydrochloride.

3. A drug comprising a compound according to claim 1.

* * * * *